United States Patent [19]

Palestrant

[11] Patent Number: 4,832,055
[45] Date of Patent: May 23, 1989

[54] MECHANICALLY LOCKING BLOOD CLOT FILTER

[76] Inventor: Aubrey M. Palestrant, 6800 N. 47th St., Paradise Valley, Ariz. 85253

[21] Appl. No.: 222,126

[22] Filed: Jul. 8, 1988

[51] Int. Cl.⁴ .............................................. A61B 17/00
[52] U.S. Cl. ................. 128/899; 128/303 R; 128/325
[58] Field of Search ............... 128/303 R, 325, 345, 128/899; 604/105

[56] References Cited

U.S. PATENT DOCUMENTS

| | | | |
|---|---|---|---|
| 3,334,629 | 8/1967 | Cohn | 128/325 R |
| 3,540,431 | 11/1970 | Mobin-Uddin et al. | 128/1 |
| 3,834,394 | 9/1974 | Hunter et al. | 128/325 |
| 3,868,956 | 3/1975 | Alfidi et al. | 128/345 |
| 3,952,747 | 8/1976 | Kimmel, Jr. | 128/303 R |
| 4,274,408 | 6/1981 | Nimrod | 128/214.4 |
| 4,425,908 | 1/1984 | Simon | 128/1 R |
| 4,430,081 | 2/1984 | Timmermans | 604/256 |
| 4,494,531 | 1/1985 | Gianturco | 128/1 R |
| 4,643,184 | 2/1987 | Mobin-Uddin et al. | 128/303 R |

FOREIGN PATENT DOCUMENTS

| | | |
|---|---|---|
| 2570288 | 1/1986 | France . |
| 2573646 | 8/1986 | France . |

OTHER PUBLICATIONS

Palestrant et al., "Comparative In Vitro Evaluation of the Nitinol Inferior Vena Cava Filter", Radiology, vol. 145, No. 2, pp. 351-355, Nov. 1982.
Simon et al., "Transvenous Devices for the Management of Pulmonary Embolism", CardioVascular and Interventional Radiology, 1980; 3: pp. 308-318.
Gunther et al., Fortschr, Rontgenstr, "Animal experiments with a new cava filter", vol. 142, No. 2, pp. 208-212 (1985).
Lund et al., Radiology, "Retrievable vena cava filter percutaneously introduced", vol. 155, No. 3, p. 831 (1985).
Lund et al., Radiology, "A new vena caval filter for percutaneous placement and retrieval: experimental study", vol. 152, pp. 369-372 (9/29/84).
Cragg et al., AJR, "A new percutaneous vena cava filter", vol. 141, pp. 601-604 (9/83).
(List continued on next page.)

Primary Examiner—Dalton L. Truluck
Attorney, Agent, or Firm—Cahill, Sutton & Thomas

[57] ABSTRACT

A blood clot filter particularly suited for filtering blood clots from blood circulating through the inferior vena cava is composed of a number of peripheral wires joined at one end by a first connector and also joined approximately at their middle portions by a second connector. The wire portions extending between the two connectors form a filter mesh, and the wire portions extending between the second connector and the free ends form filtering legs which anchor the filter. The free ends have recurved hooks for radial engagement with a blood vessel. The filter mesh is formed by mechanically approximating the two connectors resulting in the formation of overlapping loops of wire. A central core wire is fixedly secured to one of the two connectors and slidingly extends through the second of the two connectors. The central core wire is retracted to slide the two connectors together. A lock device prevents the two connectors from sliding back apart. The wire strands may initially be substantially straightened in order to permit insertion of the filter into the lumen of an angiographic catheter. The catheter is positioned at a predetermined site within the vessel using standard percutaneous angiographic techniques from the groin or neck. A pusher catheter extending within a delivery catheter pushes the filter out of the delivery catheter and into the lumen of the blood vessel. A retractor cable extends through the pusher catheter and is releasably coupled to the central core wire for retracting the same. Once the filter has been delivered into the blood vessel and the filter mesh mechanically formed, the legs are released to anchor the filter in position, and the pusher wire is disconnected.

19 Claims, 5 Drawing Sheets

OTHER PUBLICATIONS

Fadali et al., Surgery, "A filtering device for the prevention of particulate embolization during the course of cardiac surgery", vol. 64, No. 3, pp. 634–639.

MediTech Incorporated Brochure entitled "The Greenfield Vena Cava Filter, A Success Story", copyright 1986 (4 pages).

MediTech Incorporated Brochure entitled "Greenfield Vena Cava Filter System", copyright 1985, Bulletin VCF-1 (2 pages).

MediTech Incorporated publication entitled "Greenfield Vena Cava Filter System-Instructions For Use", Bulletin VCFS-5, Rev. 2/83.

Cook Inc., Advertisement, Cook "Bird's Nest" Vena Cava Filter.

L. G. Medical s.a., Advertisement, Vena Cava Filter, SP 2000, SP 2010, SP.

Cook Inc., Advertisement, Gunther Vena Cava Filter Set.

Castaneda-Zuniga et al., *Seminars in Interventional Radiology*, vol. 3, (9/86).

Wallace et al., "Inferior Vena Cava Stent Filter", *AJR*, vol. 147, pp. 1247–1250, (12/86).

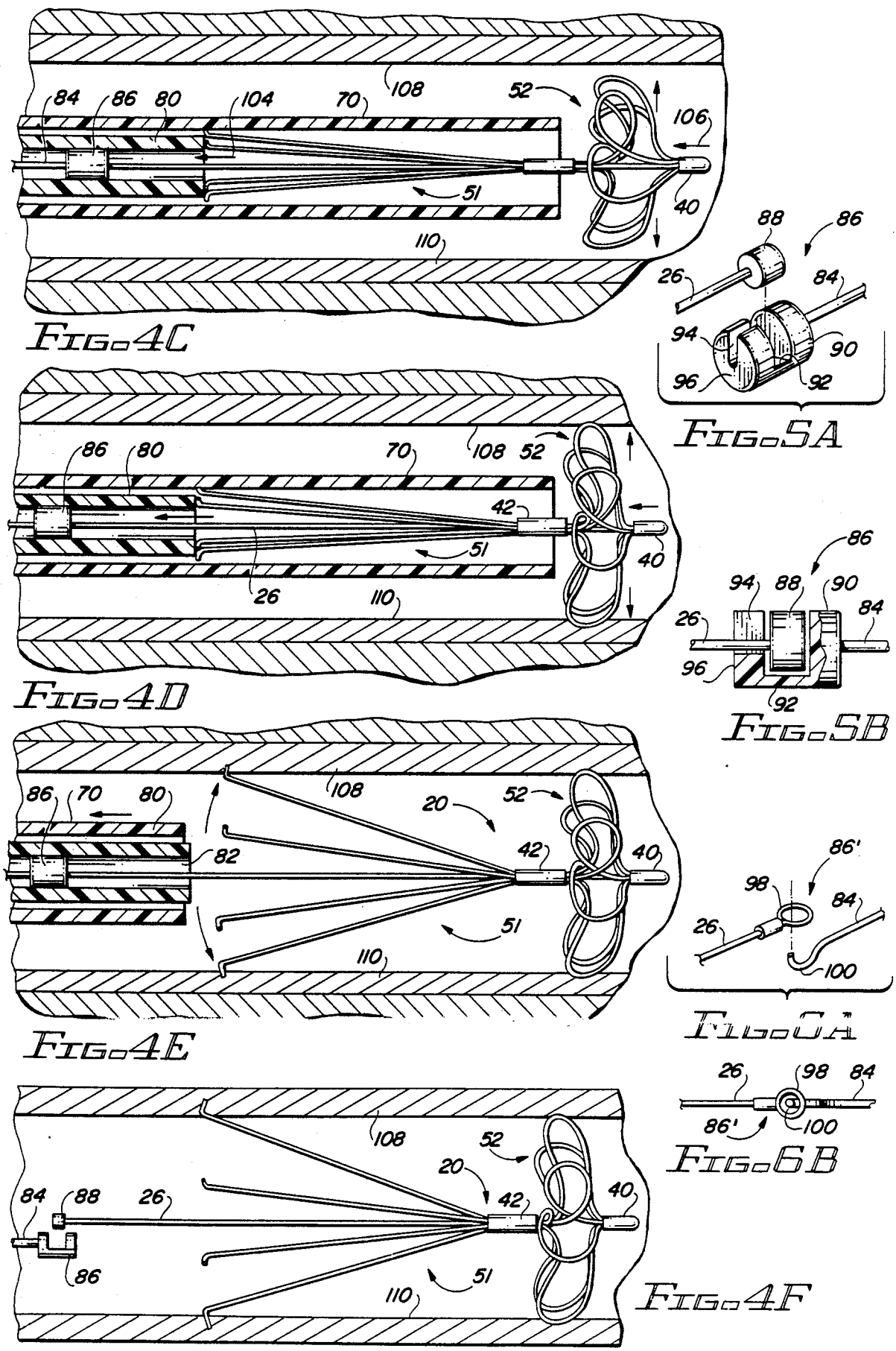

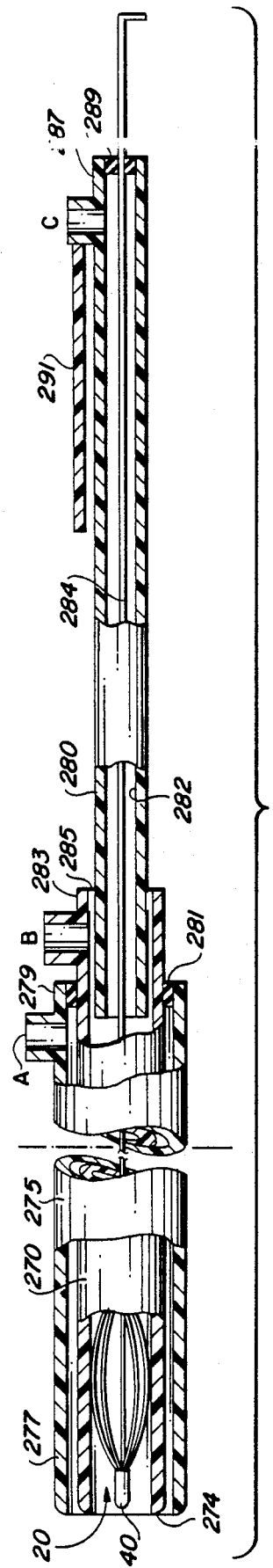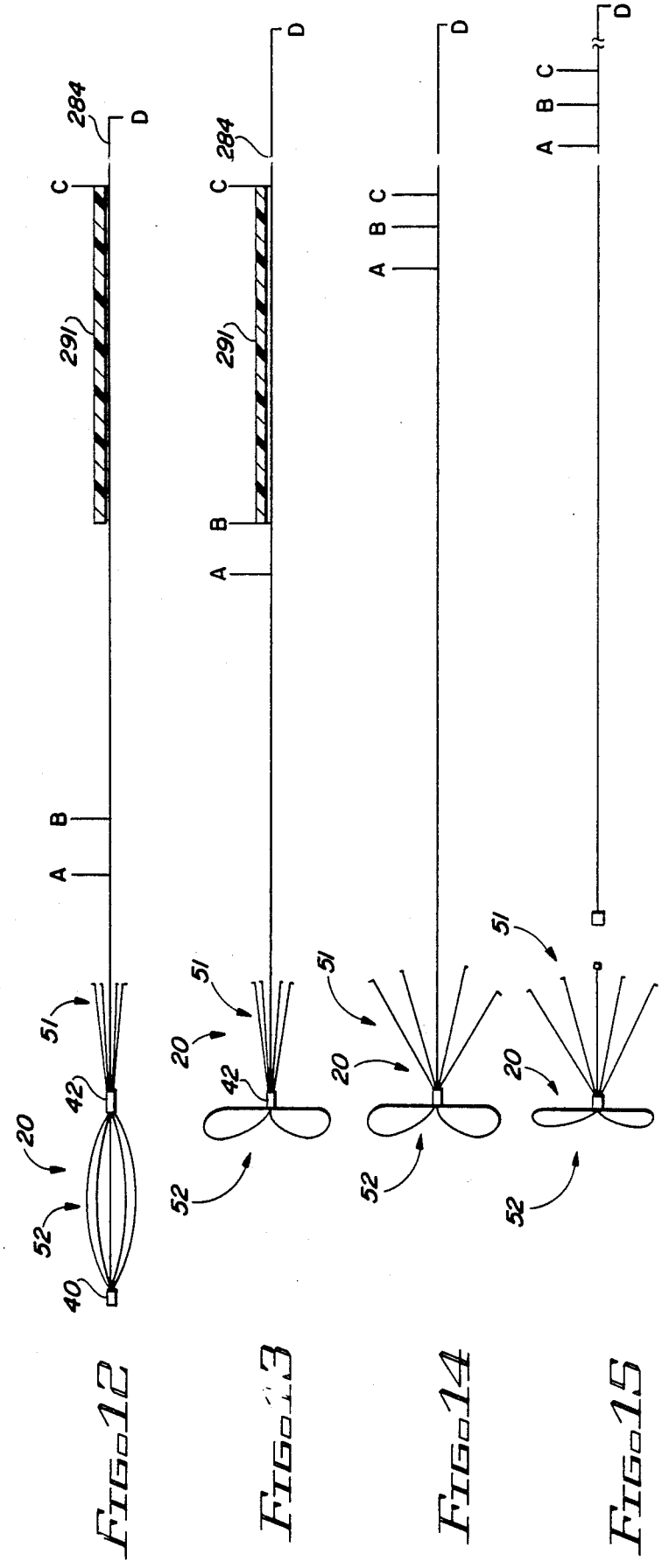

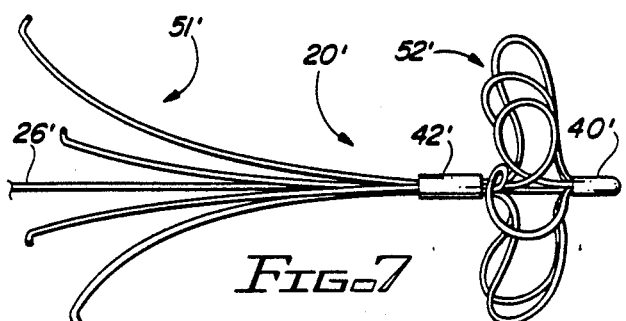
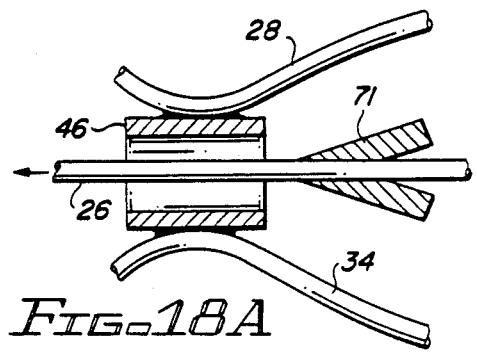
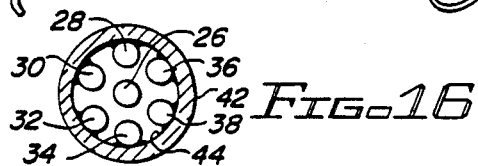
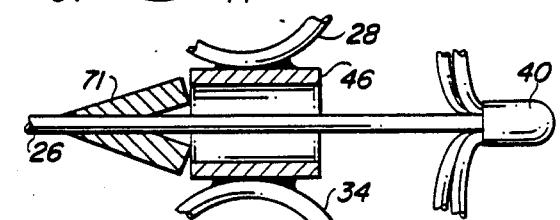
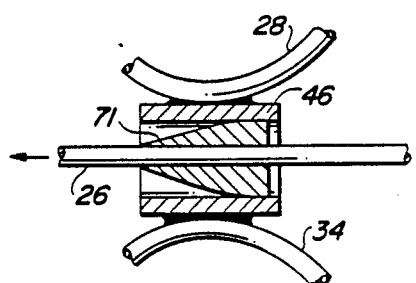
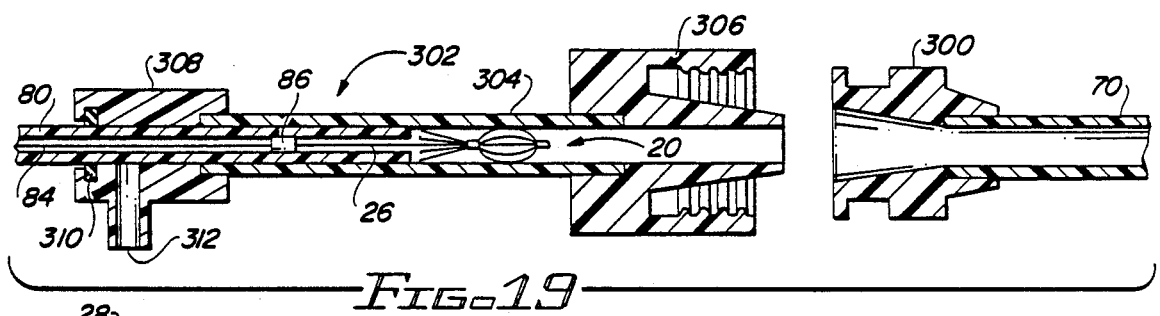
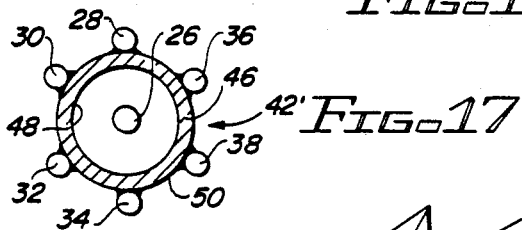
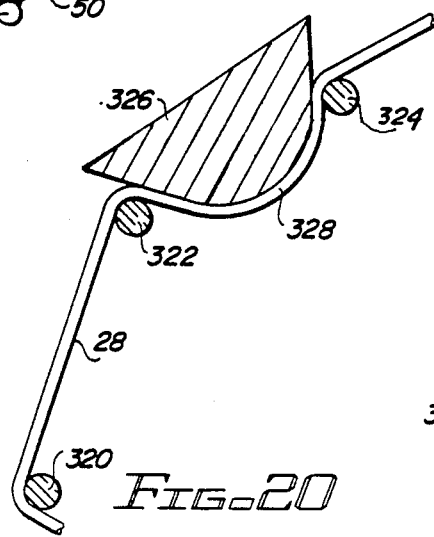
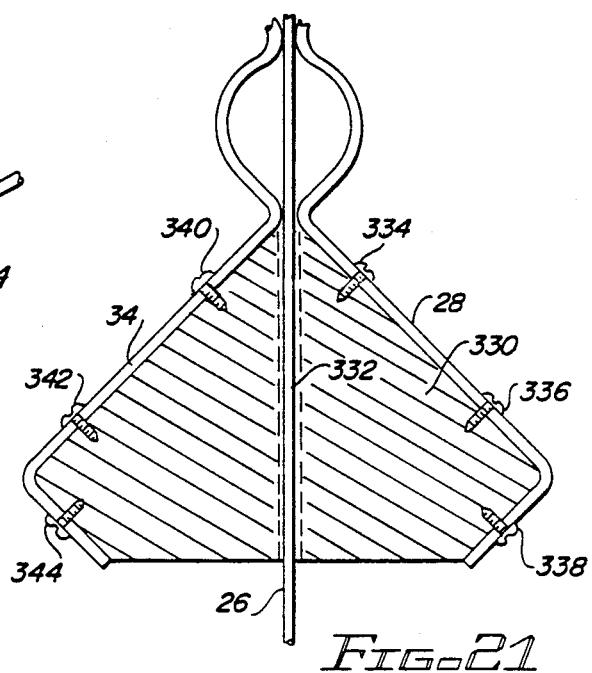

MECHANICALLY LOCKING BLOOD CLOT FILTER

BACKGROUND OF THE INVENTION

1. Field of the Invention

The present invention relates generally to devices or methods for filtering blood clots from blood vessels, and more particularly to vena cava blood clot filters and methods and apparatus for inserting such vena cava blood clot filters transvenously.

2. Background of the Invention

It is estimated that each year, approximately 750,000 patients in the United States suffer pulmonary embolism or passage of blood clots to the lungs. Of these, approximately 150,000 patients die each year from such pulmonary embolism. Most commonly, these clots originate in the veins of the pelvis or lower limbs. While most patients can be treated with blood thinning medications, these medications can jeopardize the wellbeing of some patients because of other, co-existing medical problems. Other patients exhibit recurrent embolism even while being treated with these medications. In these situations, a mechanical barrier is necessary to prevent such blood clots from travelling through the inferior vena cava to the heart and lungs.

Initially, surgical procedures were devised to form such a mechanical barrier. These procedures consisted of either tying a ligature around the inferior vena cava or placing a special clip around it. The surgery necessary to perform this procedure is extensive and requires a general anesthetic. Moreover, such surgical procedures significantly further jeopardize the health of an already ill patient.

Over the last fifteen years, several devices have been used to place a filtering device into the inferior vena cava using a transvenous route, commonly originating from the right jugular vein or from either femoral vein. For example, the method disclosed in U.S. Pat. No. 3,834,394 to Hunter, et al., uses a detachable balloon which is delivered to the inferior vena cava at the end of a catheter. The balloon and catheter are inserted into one of the veins in the neck using a surgical incision and passed to the lower inferior vena cava where the balloon is inflated. Once detached, the balloon occludes the inferior vena cava entirely, thereby preventing any flow of blood or blood clots to the heart. While insertion of this device avoids major abdominal surgery, it still requires a small surgical procedure to be performed in order to expose a neck vein. The balloon occludes the inferior vena cava completely, resulting in swelling of the lower extremities until collateral circulation develops around the balloon. With time, these collateral channels may become large enough to permit life threatening emboli to pass to the lung.

Another device for preventing pulmonary embolism but which does not require total occlusion of the inferior vena cava is an implantable cone-shaped filter device consisting of six spokes with sharpened points at the end and connected together at the other end by a central hub. A thin membrane with 4 mm. holes covers the device. The umbrella-like device is folded into a cylindrical capsule connected to the end of a catheter. This device is described in U.S. Pat. No. 3,540,431, to Mobin-Uddin. This device also requires a surgical cutdown on a major right neck vein for access to the venous system. The device and delivery capsule are positioned in the inferior vena cava and released by pushing the device out of the capsule. While the device acts as an efficient filter, approximately 60% of the patients using the Mobin-Uddin filter develop occlusion of the inferior vena cava, sometimes resulting in severe swelling of the legs. Furthermore, instances of migration of the filter to the heart have been reported; such instances present a high mortality risk.

The Hunter balloon and the Mobin-Uddin umbrella suffer from similar disadvantages in that they require a surgical procedure on the neck for exposure of a vein into which the filter may be passed. Furthermore, morbidity from occlusion of the inferior vena cava could be severe. A device which could be easily inserted from the femoral approach using standard angiographic techniques, and thereby avoid surgery, would be desirable. Ideally, the device should not totally occlude the inferior vena cava or be thrombogenic. It should also be securely anchored within the inferior vena cava to prevent migration.

U.S. Pat. No. 3,952,747, to Kimmel, discloses a blood vessel filter and filter insertion instrument which overcome some of the disadvantages of the previous two devices. The Kimmel patent describes a device which may be inserted either from the jugular or femoral approach using a surgical exposure of a major vein. The conical shaped device consists of six strands of wire each connected to a hub at one end and having recurved hooks on the other end. The device is loaded into a cylindrical delivery capsule which is connected to a catheter. The delivery capsule measures 6 mm. in diameter and 5 cm. in length. Because of its size, a surgical exposure of the vein is necessary for introduction of the delivery capsule into the vascular system. More recently, the delivery capsule has been introduced into the vascular system through a large catheter using angiographic techniques. However, this technique has been shown to significantly injure the vein at the introduction site. Sometimes it may not be possible to pass the capsule from below through tortuous pelvic veins into the inferior vena cava because of the inflexibility of the capsule. The filter engages the wall of the vein at one end and therefore often tilts to one side. It is very difficult to deliver the filter in a manner that maintains the longitudinal axis of the filter centered along the longitudinal axis of the vena cava. A tilted filter has been shown to be less efficient at capturing blood clots. Migration of the filter has not been a problem.

Another method of preventing pulmonary emboli from reaching the lungs is a device disclosed in U.S. Pat. No. 4,425,908, to Simon. This device uses the thermal shape memory properties of Nitinol to deploy the filter following delivery. The filter consists of seven wires banded at one end and also in the middle. The wires between these two points form a predetermined filter mesh derived from the thermal memory. The free-ends of the wires form anchoring points which radially engage the inferior vena cava. The device may be inserted through a jugular or femoral vein approach using standard angiographic catheters. The device relies on the thermal shape memory properties of the Nitinol wire to form an effective filter following delivery. It is not yet clear whether the filter disclosed in the Simon patent will be biocompatible in humans or if it will be thrombogenic. Concerns exist regarding its reliability when stored at different temperatures and also whether the material can be manufactured with the same consistency.

U.S. Pat. No. 4,494,531, to Gianturco, also discloses a blood vessel filter which can be inserted through angiographic catheters. The device consists of a number of strands of wire which are interconnected and wadded together to form a curly wire mesh. The filter includes a number of projections which serve as an anchoring means for anchoring the filter at a suitable body location within the inferior vena cava. Problems with the device include migration and demonstration invitro of filtering inefficiency. The random nature of the filtering mesh makes it difficult to assess the overall efficacy. Perforation of the anchoring limbs through the vena cava has also been described.

A device described by Gunther et al. in a 1985 technical article consists of a helical basket made of a number of wires and radially placed legs. Originally, it was intended to be implanted temporarily in the inferior vena cava until the patient's risk of pulmonary embolism had passed. Limited clinical experience is available.

The blood clot filter device and related delivery apparatus disclosed in the present invention, overcome the disadvantages associated with the prior art by employing a nonocclusive filter which is designed to be inserted into the vena cava using normal percutaneous catheterization techniques through a femoral or jugular approach. Thus the need for surgery is totally eliminated. The device is self-centering and has a positive mechanical locking system. This system does not require the patient to be at a given temperature in order for the filter to form its shape. Moreover, it is made of metals which have been shown to be biocompatible when used in other devices such as pacemakers and inferior vena cava filters. This is not true of the filter disclosed by Simon. The filter configuration is predetermined and not random as described by Gianturco.

Accordingly, it is an object of the present invention to provide a blood clot filter which may be implanted using normal percutaneous angiographic catheter techniques through either a femoral or jugular approach.

It is a further object of the present invention to provide a blood clot filter which is designed to be placed within the inferior vena cava below the renal veins.

It is yet a further object of the present invention to provide a blood clot filter which does not obstruct blood flow within the blood vessel at any time.

It is still a further object of the present invention to provide a blood clot filter which will not cause thrombus formation or emboli after implantation.

An additional object of the present invention is to provide a blood clot filter which is capable of being securely anchored within the blood vessel.

It is a further object of the present invention to provide a blood clot filter which forms its shape using mechanically induced conversion of straight wires into a filter mesh which may accommodate vena cavas of varying sizes.

It is another object of the present invention to provide such a blood clot filter which uses well-known biocompatible materials and which avoids reliance upon thermal memory shape characteristics, thereby providing a reliable and less expensive filter.

SUMMARY OF THE INVENTION

Briefly described, and in accordance with one embodiment thereof, the present invention relates to a blood clot filter which includes a central core wire extending along a central longitudinal axis and surrounded by a number of peripheral wires evenly spaced about the central core wire. A first connector connects the peripheral wires together at one end of the central core wire at a first fixed connection point. A second connector connects the peripheral wires together at a second connection point spaced apart from a the first connection point, the second connection point surrounding the central core wire and being slidably secured thereto. The blood clot filter includes a one-way lock device permitting the second connector to slide along the central core wire toward the first fixed connector from a first position remote from the first connector to a second position proximate the first connector. However, the lock device prevents the second connector from returning from the second proximate position back to the first remote position. The portions of the peripheral wires extending between the first and second connectors initially extend generally along the central core wire. As the second connector is advanced from the first remote position to the second proximate position, the portions of the peripheral wires extending between the first and second connectors move radially away from the central core wire to a deployed position for forming a filter mesh.

In a preferred embodiment of the present invention, the peripheral wires include leg portions which extend beyond either the first or second connector. The leg portions are biased away from the central longitudinal axis of the blood clot filter and terminate in hooked feet adapted to engage the walls of a blood vessel for anchoring the blood clot filter at a desired location therein. The leg portions provide a second filtering component in addition to the flattened filter mesh, and the leg portions, in conjunction with the flattened filter mesh, automatically center the blood clot filter within a blood vessel and prevent the same from tilting away from the central longitudinal axis.

The aforementioned second connector may be in the form of a tubular sleeve which slides over the central core wire. Each of the peripheral wires may be attached, as by welding, to the exterior wall of the tubular sleeve. In another embodiment of the present invention, the second connector is in the form of a collar through which each of the peripheral wires passes, the collar seving to collect and connect the peripheral wires to permit the same to slide along the central core wire.

A first embodiment of the present invention is primarily designed for delivery using a transfemoral approach. In this embodiment, the aforementioned first connector joins first ends of the peripheral wires together and fixedly secures the same to a first end of the core wire. The second connector joins central portions of the peripheral wires to one another for sliding along the central core wire. The second ends of the peripheral wires extend from the second connector to provide the aforementioned leg portions. The central core wire extends beyond the second connector and beyond the second ends of the peripheral wires for being retracted to deploy the flattened filter mesh.

A second embodiment of the present invention is adapted for delivery using a transjugular approach. In this embodiment, the first connector joins the central portions of the peripheral wires together and fixedly secures the same to the first end of the central core wire. The second connector joins first ends of the peripheral wires to one another and slidingly secures the same about the central core wire. The second ends of the peripheral wires extend from the first connector to form the leg portions. The central core wire extends through and beyond the second connector in a direction opposite to which the leg portions extend. The second end of the central core wire is again adapted to be retracted for deploying the filter mesh. The present invention also contemplates a filter delivery apparatus for use in conjunction with a blood clot filter of the type summarized above. The filter delivery apparatus includes a delivery catheter having a distal end for percutaneous introduction into a blood vessel, the distal end of the delivery catheter being adapted to deliver the blood clot filter within the blood vessel. A pusher catheter is slidingly received within the delivery catheter through the proximal end thereof. The distal end of the pusher catheter is advanced into the delivery catheter until it abuts the blood clot filter. Retraction of the delivery catheter, while maintaining the pusher catheter engaged with the blood clot filter causes the leading portion of the blood clot filter to be delivered from the distal end of the delivery catheter.

The filter delivery apparatus further includes a retractor cable which slidingly extends through the pusher catheter and which is releasably coupled to the retraction end of the central core wire. By pulling back on the retractor cable while maintaining the pusher catheter in abutment with the blood clot filter, the user forces the filter mesh to become locked in its deployed configuration. Further retraction of the delivery catheter while maintaining the pusher catheter fixed releases the blood clot filter entirely out of the distal end of the delivery catheter, permitting the leg portions to spring outwardly and engage the walls of the blood vessel. Retraction of both the delivery catheter and pusher catheter then permits the retractor cable to be disengaged from the retraction end of the central core wire. The delivery apparatus may then be removed, leaving the blood clot filter in the desired location.

BRIEF DESCRIPTION OF THE DRAWINGS

FIGS. 4A, 4B, 4C, 4D, 4E and 4F illustrate the delivery and deployment of the blood clot filter shown in FIG. 1 using a novel filter delivery apparatus.

FIGS. 5A and 5B are perspective and cross-sectional views, respectively, of one form of releasable coupling for releasably connecting a retraction end of a central core wire within the blood clot filter to a retractor cable within the delivery apparatus.

FIGS. 6A and 6B are perspective and top views, respectively, of a second form of releasable coupling for releasably connecting the retraction end of the central core wire within the blood clot filter to the retractor cable.

FIG. 7 is a side view of a blood clot filter similar to that shown in FIG. 1, but wherein the anchoring legs are curved rather than straight, and are of different lengths.

FIG. 11 is an alternate form of delivery apparatus including a delivery catheter in which the blood clot filter may be pre-loaded at the distal end thereof, and further including an outer catheter into which the delivery catheter may be inserted for gaining access to the blood vessel.

FIGS. 12, 13, 14 and 15 illustrate various stages in the delivery of the blood clot filter using the filter delivery apparatus shown in FIG. 11.

FIG. 16 is a sectional view of the slidable connector shown in FIG. 1 as viewed through the plane indicated by lines 15-16 in FIG. 1, wherein the slidable connector is in the form of a collar encircling the peripheral wires of the blood clot filter.

FIG. 17 is a sectional view of a slidable connector in the form of a tubular sleeve surrounding the central core wire and having a circular exterior wall to which the peripheral wires are attached.

FIGS. 18A, 18B, and 18C are sectioned views of an alternate form of lock device for mechanically locking the filter mesh of the blood clot filter in the deployed, flattened configuration.

FIG. 19 shows the proximal end of a delivery catheter, as well as a filter storage tube in which the blood clot filter may be preloaded.

FIG 20. illustrates a wire shaping jig which may be used to form the peripheral wires that are used to construct the blood clot filter.

FIG. 21 discloses an assembly jig which may be used during assembly of the blood clot filter in order to hold the central core wire and peripheral wires in place during assembly.

DETAILED DESCRIPTION OF THE PREFERRED EMBODIMENTS

Figure 1:
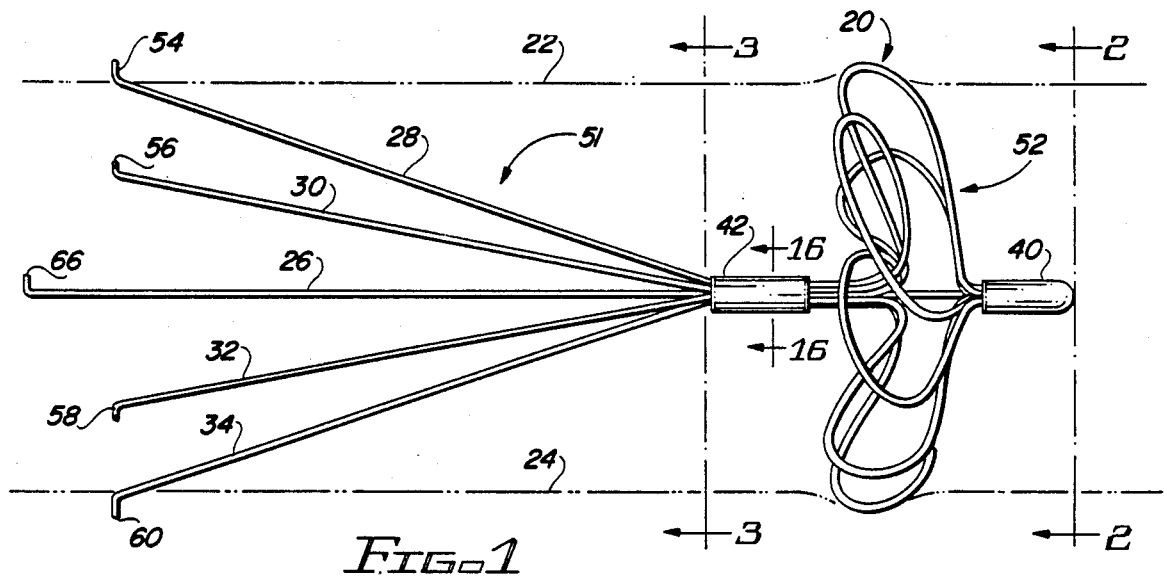
FIG. 1 is a side view of a blood clot filter constructed in accordance with the teachings of the present invention and designed for percutaneous introduction and delivery using a transfemoral approach.

In FIG. 1, a blood clot filter of the type intended for percutaneous introduction and delivery using a transfemoral approach is shown and is designated generally by reference numeral 20. Within FIG. 1, dashed lines 22 and 24 indicate the outline of an interior wall of a blood vessel, such as the inferior vena cava. Blood clot filter 20 consists essentially of a central core wire 26 which extends generally along the central longitudinal axis of blood clot filter 20, as well as six peripheral wires 28, 30, 32, 34, 36 and 38 spaced equiangularly about central core wire 26. Peripheral wires 36 and 38 are hidden from view in FIG. 1 by peripheral wires 30 and 32, respectively; however, peripheral wires 36 and 38 are visible in FIGS. 2 and 3.

In FIG. 1, a first connector 40 is shown forming a nose of blood clot filter 20. Connector 40 serves to connect together a first end of each of peripheral wires 28-38, and attaches such peripheral wires about the first end of central core wire 26 at a first connection point. Connector 40 is welded, crimped or otherwise attached to the first end of central core wire 26 and to the first ends of peripheral wires 28-38 so that a fixed connection is achieved between the central core wire and the six peripheral wires.

Still referring to FIG. 1, the six peripheral wires 28-38 are again joined along their central portions by a second connector 42. As shown best in FIG. 16, connector 42 is in the form of a tubular collar having a central opening defining an interior wall 44. Each of the peripheral wires 28-38 passes through tubular collar 42 and is secured to interior wall 44 thereof, as by welding or by other means of attachment. Thus, second connector 42 serves to connect together peripheral wires 28-38 at a second connection point spaced apart from the first connection point at first connector 40. Referring again to FIG. 16, it will be noted that central core wire 26 passes freely through the interior space defined by tubular collar 42 and the peripheral wire secured therein, thereby allowing second connector 42 to slide along central core wire 26.

Referring briefly to FIG. 17, an alternate form of second connector is shown designated by reference numeral 42'. Second connector 42' includes a tubular sleeve 46 having a central bore 48 through which central core wire 26 extends. Tubular sleeve 46 includes an exterior circular wall 50 to which each of peripheral wires 28-38 are attached, as by welding. Like connector 42 shown in FIG. 16, connector 42' shown in FIG. 17 slidingly secures the central portions of peripheral wires 28-38 about central core wire 26.

Within FIG. 1, second connector 42 is shown after having been advanced to a position relatively proximate to nose 40. The portions of peripheral wires 28-38 lying between first connector 40 and second connector 42 are shown as forming a flattened filter mesh, designated generally by reference numeral 52. Each of the portions of peripheral wires 28-38 lying between first connector 40 and second connector 42 rotates through an angle of approximately 90°-120°. As second connector 42 is advanced toward first connector 40, the portions of peripheral wires 28-38 lying between first connector 40 and second connector 42 extend radially away from central core wire 26, to a flattened, deployed position shown in FIGS. 1 and 2. As shown in FIG. 1, the extreme outermost portions of flattened filter mesh 52 engage and slightly distend the interior walls 22 and 24 of the blood vessel, thereby providing a filter mesh which extends over the entire cross-sectional area of the blood vessel and which helps locate blood clot filter 20 along the central axis of the blood vessel once the leg portions of the peripheral wires 28-38 are released. When filter mesh 52 is fully deployed, it extends substantially perpendicular to central core wire 26, and substantially perpendicular to the longitudinal axis of blood clot filter 52.

As mentioned above, the peripheral wires 28-38 rotate through an angle of approximately 90°-120° as filter mesh 52 is deployed to facilitate the flattening of the filter mesh. Peripheral wires may be pre-shaped during manufacture of blood clot filter 20 by proximating nose connector 40 and slide connector 42 and turning nose connector 40 through an angle of approximately 90°-120° while holding slide connector 42 fixed, and then heat-treating filter 20 so that the elastic memory of the peripheral wires will cause filter mesh 52 to flatten when core wire 26 is retracted.

As shown in FIG. 1, the ends of peripheral wires 28-38 lying opposite connector 40 pass outwardly through slidable connector 42 in a direction generally opposite to that of connector 40. These second ends of peripheral wires 28-38 form anchoring legs, each of which is biased away from the central longitudinal axis of blood clot filter 52. These anchoring legs collectively form a leg assembly designated by reference numeral 51. Each of the leg portions of peripheral wires 28, 30, 32, 34, 36 and 38 terminate in sharpened hooks or feet 54, 56, 58, 60, 62 and 64, respectively for engaging and becoming fixed within the interior walls 22, 24 of the blood vessel to anchor and maintain blood clot filter 52 at a desired location therein. Apart from anchoring blood clot filter 20, the leg portions of peripheral wires 28-38 independently form a blood clot filter separate and apart from flattened filter mesh 52. While leg assembly 51 is shown as being formed by extensions of peripheral wires 28-38, it will be appreciated that the wires forming such legs may be distinct from peripheral wires 28-38, and may differ in number and thickness therefrom. Thus, blood clot filter 20 provides a dual filtering system capable of filtering blood clots greater than 5 millimeters in diameter. Moreover, as mentioned above, the leg portions of peripheral wires 28-38, in combination with filter mesh 52, provide a self-centering device maintaining blood clot filter 20 centered within the blood vessel, thereby avoiding problems associated with a tilted filter.

Central core wire 26 and peripheral wires 28-38 may all be formed from stainless steel, a material which has been used extensively within the vascular system, and which is accepted by regulatory agencies and the medical community. Connectors 40 and 42 may also be made of stainless steel. Alternatively, the central core wire, peripheral wires and connectors may be formed of titanium. It is believed that a peripheral wire thickness of 0.010 inch is thick enough to withstand the impact of a blood clot against blood clot filter 20, while being thin enough to be able to be deployed into the filter mesh 52 shown in FIG. 1 without requiring excessive mechanical force. Moreover, it is believed that a wire thickness of 0.010 inch allows the filter mesh 52 to be yielding enough to accommodate a variety of caval sizes.

Figure 4A:
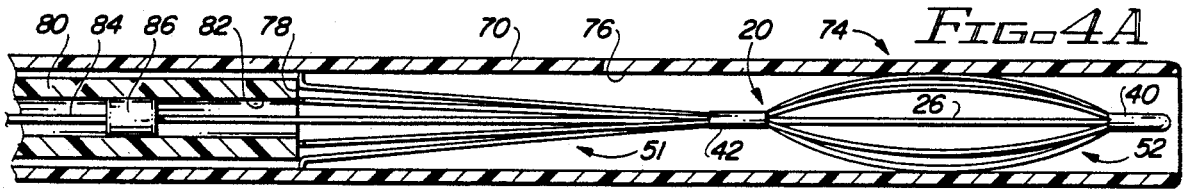
Figure 4B:
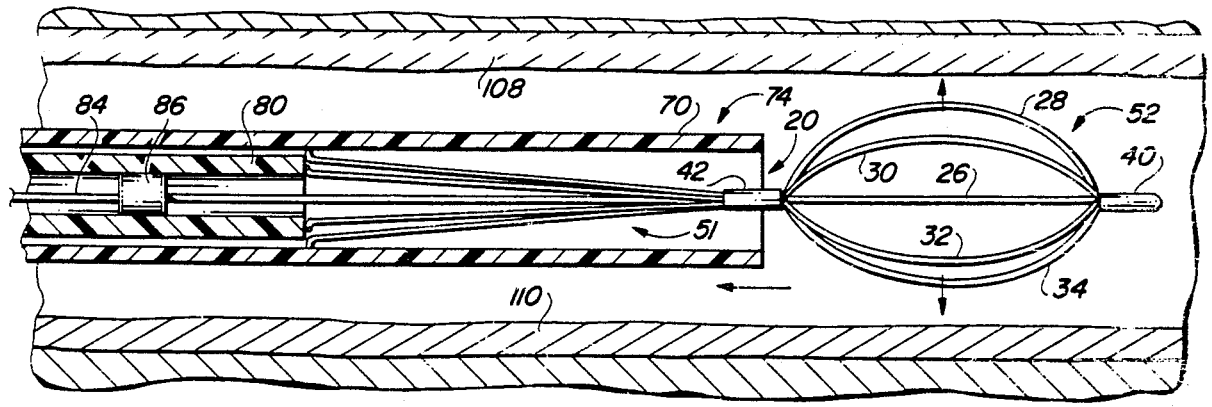

Those skilled in the art will appreciate that blood clot filter 20 must initially be provided as a slender, small diameter assembly in order to be conveniently introduced within the blood vessel by a delivery catheter. The leg portions of peripheral wires 28-38 may initially be compressed inwardly toward central core wire 26 prior to loading the device within a delivery catheter, as shown in FIG. 4A. The lengths of the various legs may be varied to facilitate loading within the delivery catheter. The filter mesh 52 is initially maintained in a compact, elongated form by initially positioning slide connector 42 at a first position relatively remote from connector 40 as shown in FIG. 4A. In this initial position, the portions of peripheral wires 28-38 extending between connector 40 and slide connector 42 lie generally along central core wire 26, as shown in FIGS. 4A and 4B. Only after filter mesh 52 is positioned within the blood vessel at the desired location is filter mesh 52 deployed outwardly to take on its flattened, mesh configuration shown in FIG. 1.

As shown in FIGS. 1 and 4A, central core wire 26 is longer than peripheral wires 28-38, and the second end of central core wire 26 opposite connector 40 includes a retractor fitting, shown in FIG. 1 as a bent or hooked end 66. When filter mesh 52 is to be deployed, central core wire 26 is retracted by pulling on retractor end 66, thereby causing first connector 40 and slide connector 42 to approach one another, and causing the portions of peripheral wires 28-38 lying between connectors 40 and 42 to extend radially outward and flatten. Were retractor end 66 to be released, the force of blood vessel walls 22 and 24 upon filter mesh 52, together with the inherent memory characteristics of fine steel wire, would tend to force connectors 40 and 42 apart back to the initial position shown in FIG. 4B. Accordingly, blood clot filter 20 includes a mechanism for locking slide connector 42 in the position shown in FIG. 1 after central core wire 26 has been retracted in order to maintain filter mesh 52 in the deployed, collapsed position. One manner in which this may be accomplished is by flattening or thickening the portion of central core wire 26 adjacent nose connector 40 whereby second connector 42' (see FIG. 17) forms a friction fit with central core wire 26 as connector 42' slides toward nose connector 40.

Figure 8A:
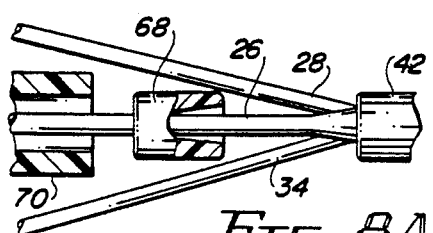
FIGS. 8A, 8B, and 8C are partially cut away detailed views of a lock device for locking the filter mesh of the blood clot filter in a deployed position and simultaneously spreading the anchoring legs to more firmly anchor the blood clot filter within the blood vessel.
Figure 8C:
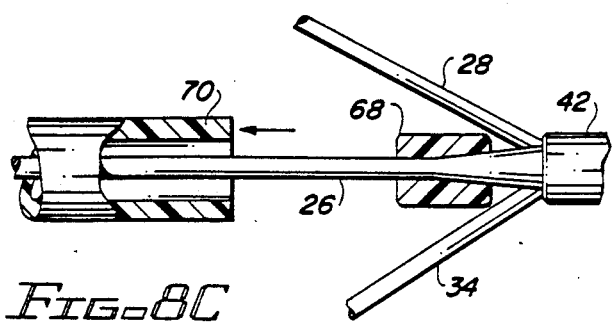
Figure 8B:
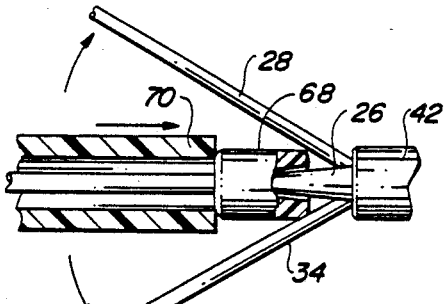

An alternate manner of locking slide connector 42 proximate nose connector 40 is shown in FIGS. 8A-8C. In FIG. 8A, lock device 68 is shown as a cylindrical member extending around central core wire 26 between second connector 42 and retractor end 66 (see FIG. 1) of central core wire 26. Lock device 68 includes a wedge-shaped interior bore of a diameter commensurate with the diameter of the central body of core wire 26. The wedge-shaped interior bore of lock device 68 opens toward nose connector 40. The diameter of core wire 26 is essentially uniform until reaching the vicinity of nose connector 40, at which point core wire 26 gradually tapers to an enlarged diameter. Lock device 68 can freely slide along central core wire 26 toward nose connector 40 (see FIG. 1) until reaching the tapered portion of core wire 26, at which point further retraction of core wire 26 causes the same to become wedged within lock device 68, thereby opposing sliding motion in the opposite direction. Prior to delivery of the blood clot filter, lock device 68 is positioned behind the feet 54-60 of leg assembly 51, thereby allowing the leg portions of peripheral wires 28 and 34 to lie generally alongside core wire 26 in a compact form. However, when central core wire 26 is being retracted, as shown in FIG. 8B, lock device 68 is simultaneously urged toward slide connector 42 and toward nose connector 40 by the distal end of a pusher catheter 70 to be described in greater detail below. Thus, lock device 68 also functions as spreader for biasing the leg portions of peripheral wires, such as 28 and 34, away from central core wire 26. In FIG. 8C, the distal end of the pusher catheter 70 is retracted. Lock device 68 thereafter opposes sliding motion of central core wire 26 relative to slide connector 42, thereby maintaining filter mesh 52 (see FIG. 1) in its deployed position, while simultaneously urging the leg portions of the peripheral wires 28-38 radially outward.

Figure 9:
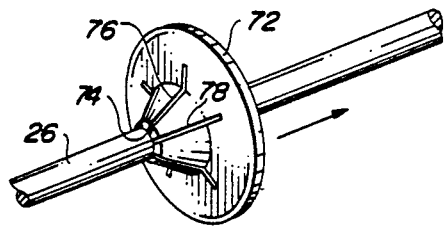
FIG. 9 is an alternate form of lock device in the form of a one-way washer which slides in one direction along the central core wire, but not in the opposite direction.

FIG. 9 shows an alternate form of a lock device. Within FIG. 9, one-way washer 72 includes a central region angled toward the leftmost side of FIG. 9. A central aperture 74 formed within the central region of washer 72 receives central core wire 26. A series of radial slots, such as 76 and 78 divide the angled central region into a series of tabs. Consequently, one-way washer may easily be moved to the right along central core wire 26 within FIG. 9. However, attempts to thereafter move one-way washer 72 to the left cause the slotted tabs to dig in to central core wire 26 and oppose further sliding movement. A lock device such as one-way washer 72 could be substituted for lock device 68 within FIGS. 8A-8C and likewise prevent central core wire 26 from sliding through slide connector 42 after having been retracted.

FIGS. 17 and 18A-18C illustrate an alternate form of lock device for the blood clot filter 20 shown in FIG. 1. As stated above in regard to FIG. 17, slide connector 42' is in the form of a tubular sleeve 46 which slidingly passes therethrough. Each of the six peripheral wires 28-38 is secured to the outer surface of tubular sleeve 46, as by welding. Referring to FIGS. 18A-18C, peripheral wires 28 and 34 are shown as being attached to the outer surface of tubular sleeve 46, as by welding. A locking device, in the form of a wedge-shaped resilient member 71 is shown fixedly secured to central core wire 26. Wedge 71 is initially to the right of tubular sleeve 46 when the blood clot filter is in its compacted form prior to deployment. The narrowest portion of which 71 lies closest to tubular sleeve 46, while the widest portion thereof is furthest from tubular sleeve 46. The widest portion of wedge 71 has a diameter or width which exceeds the internal diameter of tubular sleeve 46. However, wedge 71 is made of a sufficiently deformable material as to allow wedge 71 to be pulled through tubular sleeve 46 upon retraction of central core wire 26, as shown in FIG. 18B. Referring to FIG. 18C, central core wire 26 has been fully retracted, thereby bringing nose connector 40 of blood clot filter 20 into proximity with tubular sleeve 46 for deploying the filter mesh 52. As shown in FIG. 18C, wedge 71 now lies to the left of tubular sleeve 46, and because the widest portion of wedge 71 is wider, or of greater diameter, than tubular sleeve 46, central core wire 26 is prevented from sliding back to the right. Accordingly, the filter mesh 52 is locked in its deployed position.

FIG. 7 illustrates an alternate form of the blood clot filter shown in FIG. 1. The blood clot filter of FIG. 7 is designated generally by reference numeral 20', and like blood clot filter 20 of FIG. 1, includes a nose connector 40', a slide connector 42', a central core wire 26', and a number of peripheral wires connected between nose connector 40' and slide connector 42' to form a filter mesh 52'. The principal differences between blood clot filter 20' of FIG. 7 and blood clot filter 20 of FIG. 1 relate to the formation of the leg assembly 51'. Whereas the leg portions shown in FIG. 1 are relatively straight and of uniform length, the leg portions shown in FIG. 7 are both curved or bowed outwardly and are of differing lengths.

The manner of delivering blood clot filter 20 of FIG. 1 using a transfemoral approach will now be described with reference to FIGS. 4A-4F wherein a novel filter delivery apparatus is shown. FIG. 4A shows blood clot filter 20 in a compacted position received within the distal end 74 of a delivery catheter 70. Slide connector 42 of blood clot filter 20 is remote from nose connector 40 to elongate filter mesh 52, and the hooked end of the leg portions of peripheral wires 28-38 are compressed against the interior wall 76 of delivery catheter 70. Not shown in FIG. 4A is the proximal end of delivery catheter 70 which lies opposite distal end 74 thereof. Inserted through the proximal end of delivery catheter 70 is a semi-rigid pusher catheter 80, the distal end 78 of which is visible in FIG. 4A. Not shown within FIG. 4A is the proximal end of pusher catheter 78 which extends from the proximal end of delivery catheter 70. Pusher catheter 80 is slidingly received within delivery catheter 70, and the distal end 78 of pusher catheter 80 is adapted to abut hooked end portions 54-64 of peripheral wires 28-38.

Still referring to FIG. 4A, central core wire 26 is shown extending within the central bore 82 of pusher catheter 80 and is releasably coupled to a retractor cable 84 by a releasable coupling mechanism 86. Retractor cable 84 slidingly extends through bore 82 of pusher catheter 80. Not shown in FIG. 4A is the proximal end of retractor cable 84 which extends outwardly from the proximal end of pusher cable 80 so that it may be retracted and otherwise manipulated by a physician. Releasable coupling mechanism 86 is required since retractor cable 84 must be disengaged from central core wire 26 of blood clot filter 20 once the blood clot filter has been properly positioned and deployed.

Referring briefly to FIGS. 5A and 5B, releasable coupling mechanism 86 is shown as a cylindrical nub 88 secured to the end of central core wire 26, together with a slotted, cylindrical catch 90 secured to the distal end of retractor cable 84. Catch 90 has a diameter commensurate with the diameter of the interior bore 82 of psher catheter 80. Catch 90 includes a lateral slot 92 having a depth and width commensurate with nub 88 for allowing nub 88 to be releasably captured therein. In addition, a radial slot 94 extends through the front face 96 of catch 90 and extending to lateral slot 92 for permitting central core wire 26 to extend through the front face 96 of catch 90. It should be appreciated that when nub 88 rests within catch 90, and when catch 90 lies within pusher catheter 80, central core wire 26 and retractor cable 84 are effectively secured together. However, when it is desired to disengage retractor cable 84 from central core wire 26, the user need only retract pusher catheter 80 and delivery catheter 70 for allowing catch 90 to disengage nub 88.

An alternate releasable coupling mechanism 86' is shown in FIGS. 6A and 6B. Within FIG. 6A, central core wire 26 may terminate in a looped connector 98 preferably having a width commensurate with the internal diameter of bore 82 of pusher catheter 80. The distal end of retractor cable 84 includes a hooked end 100, also having lateral dimensions commensurate with the internal diameter of bore 82 of pusher catheter 80. Prior to delivery of the blood clot filter, hook 100 is inserted within looped connector 98, which remain engaged with one another so long as they lie within bore 82 of pusher catheter 80. After the filter mesh of the blood clot filter has been deployed by retracting central core wire 26, both pusher catheter 80 and delivery catheter 70 can be retracted for permitting hooked end 100 of retractor cable 84 to disengage looped connector 98 of central core wire 26.

Referring again to FIG. 4A, blood clot filter 20 is shown as being contained fully within distal end 74 of delivery catheter 70. Delivery catheter 70 may be, for example, a 10 or 12 French Teflon catheter, and may be introduced into the blood vessel using the standard Selldinger angiographic technique. To position a flexible catheter within a blood vessel using the so-claled Selldinger technique, a needle is first inserted into the blood vessel, a guide wire is then threaded through the needle, and the needle is then withdrawn leaving the guide wire in place. Delivery catheter 70 is an open-ended catheter, and a tapered, snug-fitting angiographic catheter (not shown) may be inserted within delivery catheter 70 to facilitate the passage of delivery catheter 70 through the blood vessel. Delivery catheter 70 and the tapered angiographic catheter therein are then inserted into the blood vessel over the guide wire. Delivery catheter 70 may be advanced through the blood vessel until distal end 74 is approximately at the position at which the blood clot filter 20 is to be delivered. Following placement of delivery catheter 70 within the blood vessel, the inner tapered angiographic catheter and guide wire are withdrawn.

FIG. 19 illustrates a filter storage tube into which blood clot filter 20 may be preloaded for being advanced into delivery catheter 70 after delivery catheter 70 has been placed within the blood vessel. Within FIG. 19, delivery catheter 70 includes a female luer lock connector 300 at its proximal end. The filter storage tube is designated generally by reference numeral 302 and includes a short section of tubing 304 having approximately the same internal diameter as delivery catheter 70. Shown within filter storage tube 304 is blood clot filter 20. A first end of filter storage tube 302 includes a male luer lock connector 306 adapted to screw onto female connector 300. The opposite end of filter storage tube 304 is integrally joined with a molded fitting 308 which includes a deformable elastomeric seal 310, as well as an infusion port 312. The distal end of pusher catheter 80 extends into filter storage tube 302 through deformable seal 310, and retractor cable 84 extends within pusher catheter 80 and is coupled to core wire 26 by releasable coupling mechanism 86. Once delivery catheter 70 has been advanced into the blood vessel so that its distal end is at the appropriate delivery site, an infusion line is connected to infusion port 312, and male luer connector 306 is then coupled to female luer connector 300. Pusher catheter 80 and retractor cable 84 are then advanced as a unit to push blood clot filter 20 out of filter storage tube 302 and into delivery catheter 70. Pusher catheter 80 and retractor cable 84 are further advanced until blood clot filter 20 has been pushed to the distal end of delivery catheter 70. The remaining steps for delivering blood clot filter 20 within the blood vessel are described below.

The next step in deploying blood clot filter 20 is to partially retract delivery catheter 70 while leaving semi-rigid pusher catheter 80 fixed, until the distal end 74 of delivery catheter 70 has been retracted to approximately the location of slide connector 42. The natural springiness of the peripheral wires 28-34 of the filter mesh 52 causes each of the peripheral wires to move somewhat further apart from central core wire 26 as compared with their compacted configurations as shown in FIG. 4A. Turning to FIG. 4C, the next step in deploying filter mesh 52 is to maintain the positions of delivery catheter 70 and pusher catheter 80 fixed, with the hooked feet 54-60 of blood clot filter 20 abutting distal end 78 of pusher catheter 80. The proximal end (not shown) of retractor cable 84 is then slowly retracted by the operaotr. As retractor cable 84 is retracted, releasable coupling mechanism 86 causes central core wire 26 to be pulled to the left (relative to FIG. 4C), as indicated by the arrow designated by reference numeral 104. While central core wire 26 slidably extends through slide connector 42, central core wire 26 is rigidly attached to nose connector 40. Accordingly, as central core wire 26 is retracted, nose connector 40 also moves to the left, as indicated by the arrow designated by reference numeral 106. As nose connector 40 is brought closer to slide connector 42, the peripheral wires making up filter mesh 52 are each forced radially outward toward the inner walls 108 and 110 of the blood vessel. Continued retraction of retractor cable 84 and central core wire 26, as shown in FIG. 4D, causes filter mesh 52 to become fully deployed, with nose connector 40 being positioned relatively proximate to slide connector 42. As shown in FIG. 4D, the outermost portions of filter mesh 52 become engaged with interior walls 108 and 110 of the blood vessel upon filter mesh 52 becoming fully deployed. As explained above, slide connector 42 has associated therewith a lock device which prevents central core wire 26 from later sliding to the right (relative to FIG. 4D) through slide connector 42, and nose connector 40 is thereby maintained closely proximate to slide connector 42.

The next step in deploying blood clot filter 20 is to further retract delivery catheter 70, as shown in FIG. 4E, to expose the leg portions thereof and allow the same to spring outward for allowing the hooked ends thereof to engage internal walls 108 and 110 of the blood vessel as shown in FIG. 4E. The leg assembly 51 of blood clot filter 20 forms a filter in additon to filter mesh 52. Moreover, because blood clot filter 20 engages the internal walls 108 and 110 of the blood vessel both along the periphery of filter mesh 52 and the hooked ends of the leg portions, blood clot filter 20 is positioned centrally along the longitudinal axis of the blood vessel.

The last step in the delivery of blood clot filter 20 is shown in FIG. 4F wherein both delivery catheter 70 and pusher catheter 80 are retracted, leaving only retractor cable 84 in the same position shown as in FIG. 4E. Retraction of both delivery catheter 70 and pusher catheter 80 releases coupling mechanism 86 from internal bore 82 of pusher catheter 80 and permits coupling mechanism 86 to be released from nub 88 of central of core wire 26. Retractor cable 84 is then retracted back within internal bore 82 of pusher catheter 80, and the delivery system is then fully removed, leaving blood clot filter 20 properly positioned within the blood vessel at the desired location.

Figure 10A:
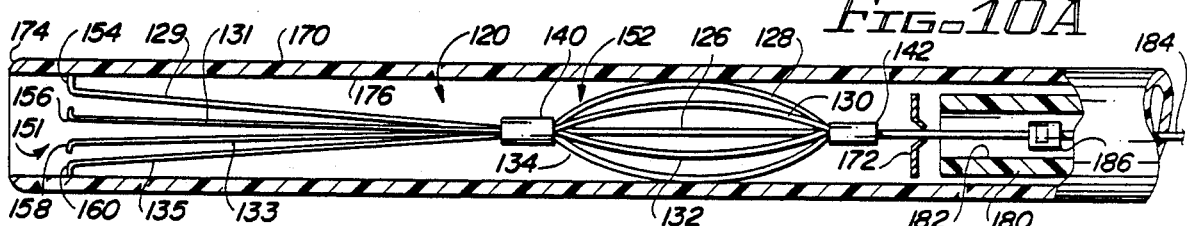
FIGS. 10A, 10B, and 10C are cross-sectional side views of an alternate form of blood clot filter intended for percutaneous introduction and delivery using a transjugular approach, together with a delivery apparatus for introducing such blood clot filter.
Figure 10B:
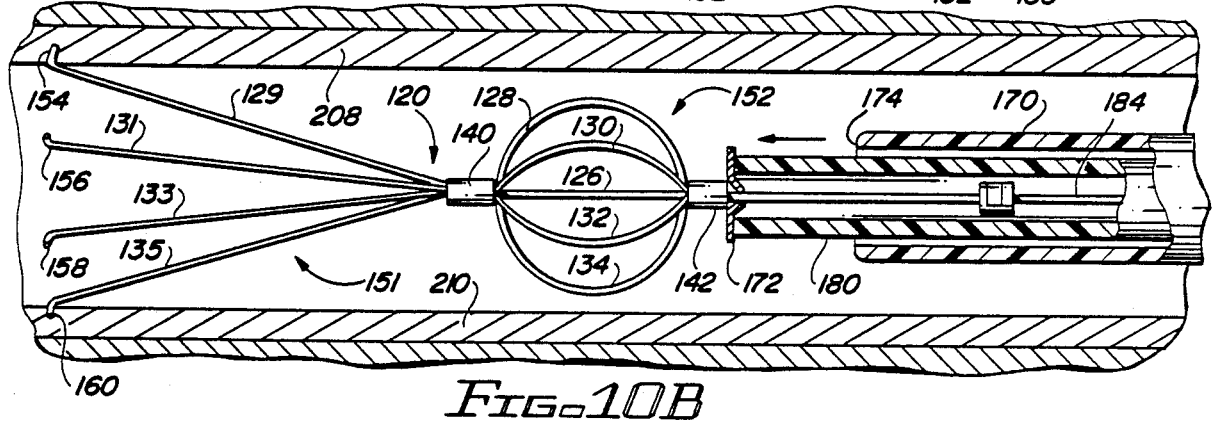
Figure 10C:
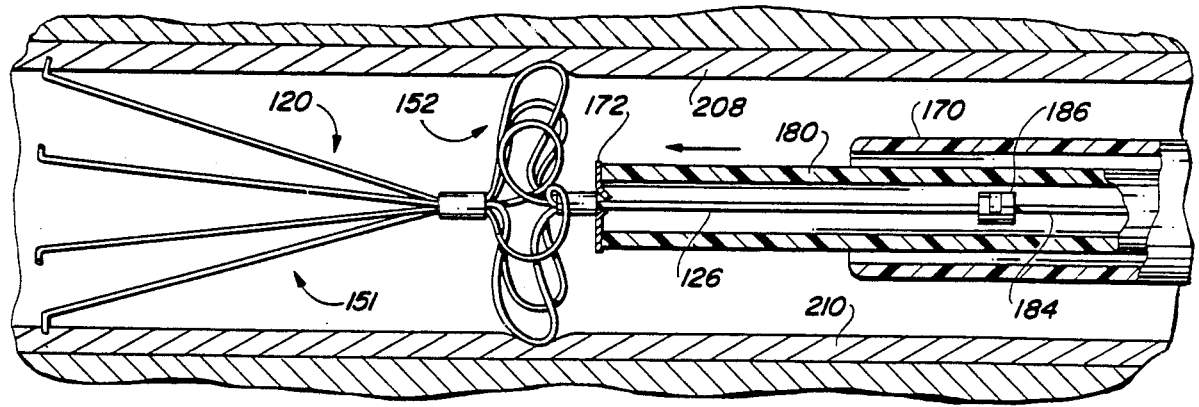

FIGS. 10A–10C illustrate an alternate embodiment of the present invention including a blood clot filter 120 designed for jugular delivery. As shown in FIG. 10A, blood clot filter 120 includes a central core wire 126 having a first end rigidly attached to a first connector 140. Central core wire 126 extends along the central longitudinal axis of blood clot filter 120 and passes through the central bore of a slide connector 142. A one-way lock washer 172, similar to that shown in FIG. 9, has a central bore through which core wire 126 extends. Washer 172 is adapted to permit core wire 126 to slide therethrough to the right (relative to FIG. 10A), but to resist sliding movement of central core wire 126 to the left. A plurality of peripheral wires, including those peripheral wires 128, 130, 132, and 134 visible in 10A each have a first end attached to slide connector 142, and are each attached to connector 140. Peripheral wires 128–134 are shown in FIG. 10A in their compacted position loaded within a jugular delivery catheter 170. Each of the peripheral wires 128–134 extends generally along and parallel to central core wire 126, as shown in FIG. 10A.

Also extending to the left of connector 140 is a leg assembly 141 consisting of, for example, six wire legs, including those visible in FIG. 10A and designated by reference numerals 129, 131, 133, and 135. Each of such legs 129–135 has a first end secured to connector 140 and a second end opposite thereto formed into hooked feet 154, 156, 158, and 160, respectively, for engaging the walls of a blood vessel into which blood clot filter 120 is to be positioned. As mentioned above, leg portions 129–135 may simply be continuations of the respective peripheral wires 128–134 which make up the filter mesh 152.

To deliver blood clot filter 120 using the jugular delivery technique, delivery catheter 170 is introduced into the blood vessel and advanced through the blood vessel until the distal end 174 of delivery catheter 170 is located at approximately the position at which blood clot filter 120 is to be delivered. Blood clot filter 120 is positioned within the distal end of delivery catheter 170, as shown in FIG. 10A, either by pushing blood clot filter 120 along the length of delivery catheter 170 from the proximal end thereof, or by preloading blood clot filter 120 within the distal end of delivery catheter 170, in the manner described below. Within FIG. 10A, semi-rigid pusher catheter 180 is shown extending within the internal bore 176 of delivery catheter 170. Though not shown, the proximal end of pusher catheter 180 extends fully through the proximal end of delivery catheter 170 so that it may be manipulated by a physician. Pusher catheter 180 has a diameter commensurate with that of one-way washer 172, and the distal end of pusher catheter 180 is adapted to abut and push against washer 172. Central core wire 126 extends within internal bore 182 of pusher catheter 180 and is releasably connected with releasable coupling mechanism 186. The distal end of retractor cable 184 is also coupled to releasable coupling mechanism 186. Retractor cable 184 extends fully through the internal bore 182 of pusher catheter 180 and protrudes from the proximal end thereof for allowing the physician to retract retractor cable 184.

During delivery of blood clot filter 120, delivery catheter 170 is retracted to the right, initially permitting legs 129–135 of leg assembly 151 to spring outward, with the hooked ends 154–160 thereof engaging the internal walls 208 and 210 of the blood vessel. Further retraction of delivery catheter 170 permits the peripheral wires 128–134 of filter mesh 152 to bow outwardly, as shown in FIG. 10B.

The next step in deploying blood clot filter 120 is to advance pusher catheter 180 to the left, while fixing the position of retractor cable 184. It is important to fix the position of retractor cable 184 to maintain connector 140 in a fixed position relative to the blood vessel, and thereby avoid movement of hooked ends 154–160, as such longitudinal movement could cause trauma to the walls 208 and 210 of the blood vessel. As pusher catheter 180 is advanced to the left, it advances washer 172 to the left along central core wire 126. As washer 172 advances to the left, it moves slide connector 142 into proximity with connector 140, thereby causing peripheral wires 128–134 to become radially extended to form filter mesh 152, as shown in FIG. 10C. When pusher catheter 180 is fully advanced to the left, the outermost portions of filter mesh 152 engage the walls 208 and 210 of the blood vessel. Pusher catheter 180 is then retracted; as pusher catheter 180 is retracted, washer 172 becomes locked against central core wire 126 and thereby maintains filter mesh 152 within the deployed position shown in FIG. 10C. Both pusher catheter 180 and delivery catheter 170 are retracted to the right (relative to FIG. 10C) for exposing releasable coupling mechanism 186, thereby allowing central core 126 to be disengaged from retractor cable 184, as was described above in regard to FIG. 4F. Retractor cable 184, pusher catheter 180, and delivery catheter 170 may then be fully retracted, leaving blood clot filter 152 in the desired location.

As explained above with respect to FIG. 19, blood clot filter 20 can be loaded into the proximal end of delivery catheter 70 using a filter storage tube that couples to the proximal end of delivery catheter 70. However, blood clot filter 20 must then be pushed along the delivery catheter to the distal end thereof; during this procedure, the hooked ends of the blood clot filter legs scrape against the inner wall of the delivery catheter and could dislodge particles therefrom. In order to avoid the need to push the blood clot filter along the entire length of the delivery catheter, the alternate form of filter delivery system shown in FIG. 11 may be used.

Within FIG. 11, blood clot filter 20 is of the same type shown in FIG. 1, and delivery catheter 270 is of essentially the same type as delivery catheter 70 of FIG. 4A. Similarly, pusher catheter 280 and retractor cable 284 correspond to the pusher catheter 80 and retractor cable 84 shown in FIG. 4A. However, as shown in FIG. 11, delivery catheter 270 is inserted through an outer catheter 275 which has a distal end 277 and a proximal end 279. The distal end 277 of outer catheter 275 is percutaneously introduced into a blood vessel using the aforementioned Selldinger technique prior to insertion of delivery catheter 270 therein. After outer catheter 275 is introduced within the blood vessel, delivery catheter 270 is inserted into outer catheter 275 from the proximal end 279 thereof. The proximal end 279 of outer catheter 275 includes a deformable elastomeric seal 281 which permits delivery catheter 270 to be slidingly received thereby while forming a fluid tight seal therearound. The proximal end 279 of outer catheter 275 also includes an infusion port A extending perpendicularly to the longitudinal axis of outer catheter 275 for permitting saline solution to be infused therein, thereby preventing the patient's blood from filling the internal bore of outer catheter 275 and forming blood clots. Similarly, the proximal end 283 of delivery catheter 270 includes a deformable elastomeric seal 285 for slidingly receiving the distal end of pusher catheter 280 and forming a fluid tight seal therearound. The proximal end 283 of delivery catheter 270 also includes an infusion port B into which saline solution may be infused to prevent the patient's blood from collecting within the internal bore of delivery catheter 270 and forming blood clots.

Similarly, pusher catheter 282 has a proximal end 287 provided with a deformable elastomeric seal 289 which slidingly receives the retractor cable 284 and forms a fluid tight seal therearound. The proximal end 287 of pusher catheter 280 also includes an infusion port C for infusion of saline solution to prevent the patient's blood from collecting within the internal bore of pusher catheter 280 and forming blood clots. The proximal end of retractor cable 284 may include a downwardly turned handle D for convenient operation of retractor cable 284.

The delivery system shown in FIG. 11 permits blood clot filter 20 to be preloaded into the distal end of delivery catheter 270 before delivery catheter 270 is inserted into outer catheter 275. This is avoids the need to insert blood clot filter 20 into delivery catheter 270 from the proximal end thereof. As shown in FIG. 11, a removable stop 291 may be releasably coupled, as by a clip (not shown) to pusher catheter 280 for defining a fixed space or distance between infusion port C and the leftmost end of stop 291. The importance of the fixed space created by stop 291 is explained in greater detail below in conjunction with FIGS. 12-15.

FIGS. 12-15 illustrate, in schematic form, the series of steps followed in using the delivery system in FIG. 11. As shown in FIG. 12, blood clot filter 20 is initially disposed in its compacted position, similar to that shown in FIG. 11. In FIG. 13, both outer catheter 275 and delivery catheter 270 are retracted until infusion port B abuts the leftmost end of stop 291. Similarly, outer catheter 275 is retracted until the proximal end 279 thereof abuts infusion port B of delivery catheter 270. Stop 291 is of a sufficient length to permit delivery catheter 270 and outer catheter 275 to be withdrawn to the extent that the peripheral wires forming the filter mesh are no longer encased by delivery catheter 270, while the leg assembly 51 of blood clot filter 20 remains encased by delivery catheter 270. As shown in FIG. 13, retractor cable 284 is then retracted while holding the proximal end 287 of pusher catheter 280 fixed, thereby deploying filter mesh 52 of blood clot filter 20. The next step involves removing stop 291 and thereafter retracting both delivery catheter 270 and outer catheter 275 until the proximal end 283 of delivery catheter 270 abuts infusion port C, and similarly, the proximal end 279 of outer catheter 275 abuts infusion port B, as shown in FIG. 14. This operation further retracts both the distal ends of delivery catheter 270 and outer catheter 275, thereby permitting leg assembly 51 of blood clot filter 20 to spring outwardly and engage the walls of the blood vessel. Referring to FIG. 15, the next step of the operation is to retract pusher catheter 280, as well as delivery catheter 270 and outer catheter 275, in order to permit the distal end of retractor cable 284 to be released from the central core wire of blood clot filter 20, as is indicated within FIG. 15. With blood clot filter 20 then properly positioned, the entire delivery system is fully retracted out of the blood vessel.

Figure 2:
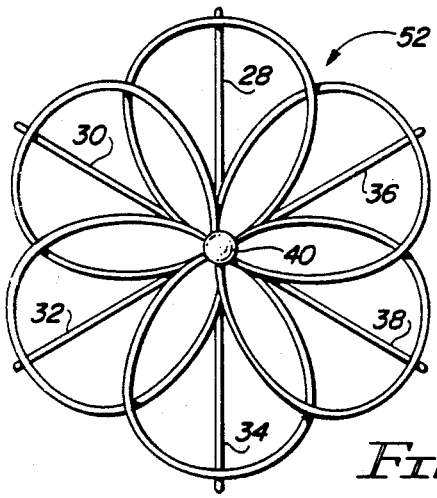
FIG. 2 is a frontal view as viewed through the plane indicated by lines 2—2 in FIG. 1.
Figure 3:
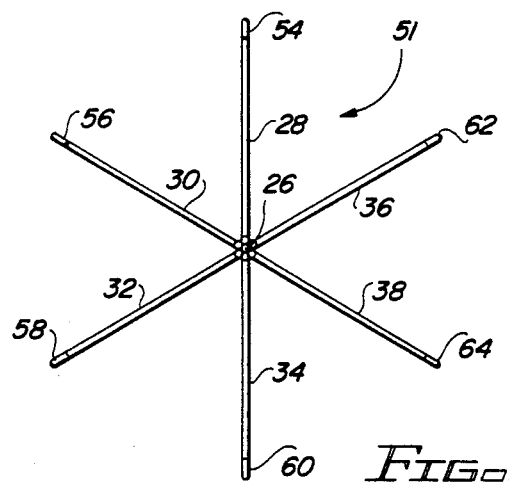
FIG. 3 is a sectioned view of the filter device shown in FIG. 1, as viewed from the plane indicated by lines 3—3 in FIG. 1 and illustrating six anchoring legs for anchoring the blood clot filter at a desired location in a blood vessel.

FIG. 20 illustrates a wire shaping jig which may be used for pre-shaping each of the peripheral wires 28-38 shown in FIGS. 1-3. As shown in FIG. 20, the wire shaping jig includes three circular pegs 320, 322, and 324. Pegs 320 and 322 are spaced apart from one another by approximately the distance between second connector 42 and hooked end 54 shown in FIG. 1. Pegs 322 and 324 are spaced apart from another by approximately the distance shown between nose connector 40 and slide connector 42 shown in FIG. 4B. The wire shaping jig also includes a form 326 having a semi-circular curved surface 328 adapted to advance between pegs 322 and 324. As shown in FIG. 20, peripheral wire 28 is placed against pegs 320, 322 and 324. Form 326 is then advanced against peripheral wire 28 and causing the same to be pushed through the space between pegs 322 and 324. Form 326 is further advanced until the curved surface 328 thereof is closely proximate pegs 322 and 324. The ends of peripheral wire 28 are then bent around pegs 320 and 324. The portion extending beyond peg 320 is later clipped to form the hooked end 54 of the anchoring leg. Similarly, the portion extending beyond peg 324 is later clipped and attached to nose connector 40 of blood clot filter 20.

FIG. 21 illustrates an assembly jig which may be used to support the central core wire 26 centrally of the plurality of peripheral wires to facilitate the connection of the peripheral wires about the central core wire. As shown in FIG. 21, the mounting jig 330 is generally cone shaped and includes a central bore 332 through which central core wire 26 extends. A set of three screws 334, 336 and 338 threadedly engage the cone shaped mounting jig. The slotted heads of screws 334, 336 and 338 may be slightly loosened for allowing the peripheral wire 28 to extend under such slotted heads. Screws 334, 336 and 338 are then tightened to hold peripheral wire 28 in place, with the central bend thereof which was formed about peg 322 (see FIG. 20) positioned at the tip of the cone shaped jig 330. Similarly, other sets of mounting screws, such as 340, 342 and 344 are also provided for releasably supporting the other peripheral wires, such as peripheral wire 34. With all six wires secured to mounting jig 330 and spaced equiangularly about central core wire 26, it is relatively easy to weld or clip together the upper ends of the peripheral wires 28-38 with the upper end of central core wire 26, as within nose connector 40 (see FIG. 1). It is also then relatively easy to join together the peripheral wires at the upper tip of the cone-shaped jig 330, as with a slide connector 42 (see FIG. 1). As mentioned above, it may be desirable to rotate the nose connector through an angle of 90°-120°, and perhaps to impart a heat treatment to the wires in order to pre-shape the filter mesh so that it will flatten when the central core wire is retracted. The aforementioned rotation of the nose connector may easily be performed before the central core wire 26 and peripheral wires 28-38 are removed from assembly jig 330. The extra wire lengths extending below screws 336 and 342 may thereafter be clipped and the ends shaped to provide hooked ends on the ends of the anchoring legs.

While the present invention has been described in accordance with a preferred embodiment thereof, the description is for illustrative purposes only and should not be construed as limiting the scope of the invention. Various changes and modifications may be made by those skilled in the art without departing from the true spirit and scope of the invention as defined by the appended claims.

I claim:

1. A blood clot filter comprising in combination:
   a. a core wire extending along a central longitudinal axis of said blood clot filter;
   b. a plurality of peripheral wires extending generally about and spaced around said core wire;
   c. first connector means for connecting together said plurality of peripheral wires at a first connection point, said core wire lying within said plurality of peripheral wires at said first connection point, said first connector means fixedly securing said plurality of peripheral wires to said core wire lying therein;
   d. second connector means for connecting together said plurality of peripheral wires at a second connection point spaced apart from said first connection point, said core wire lying within said plurality of peripheral wires at said second connection point, said second connection means slidingly securing said plurality of peripheral wires about said core wire lying therein;
   e. locking means permitting said connector means to slide along said core wire in a first direction toward said first connector means from a first remote position to a second proximate position, said locking means preventing said second connector means from sliding along said core wire in a direction opposite to said first direction from said second proximate position back to said first remote position; and
   f. said plurality of peripheral wires each including a wire portion extending between said first and second connector means and lying generally along said core wire when said second connector means is in said first remote position, said wire portions moving radially away from said core wire to a deployed position for forming a generally flattened filter mesh as said second connector means advances to said second proximate position.

2. The blood clot filter recited by claim 1 wherein each of said plurality of peripheral wires includes a leg portion extending from one of said first and second connector means in a direction generally opposite to the other of said first and second connector means, each of said leg portions being biased away from the central longitudinal axis of said blood clot filter, each of said leg portions having a foot at an end thereof for engaging an interior wall of a blood vessel to maintain said blood clot filter at a desired location within said blood vessel, and to maintain said blood clot filter centered within said blood vessel.

3. The blood clot filter recited by claim 2 including spreader means disposed between said leg portions and said core wire for biasing said leg portions away from the central longitudinal axis of said blood clot filter.

4. The blood clot filter recited by claim 1 further including a plurality of legs spaced about said core wire, each of said legs having a first end coupled to one of said first and second connector means and a second end opposite the first end, the second end of each of said plurality of legs having a foot for engaging an interior wall of a blood vessel to maintain said blood clot filter at a desired location within said blood vessel, and to maintain said blood clot filter centered within said blood vessel.

5. The blood clot filter recited by claim 4 including spreader means disposed between said plurality of legs and said core wire for biasing said leg portions away from the central longitudinal axis of said blood clot filter.

6. The blood clot filter recited by claim 1 wherein said second connector means comprises a sleeve through which said core wire extends, said sleeve having an exterior circular wall, and each of said plurality of peripheral wires being connected to said exterior circular wall.

7. The blood clot filter recited by claim 1 wherein said second connector means comprises a collar having a central opening, each of said plurality of peripheral wires extending through the central opening of said collar and being secured to said collar.

8. The blood clot filter recited by claim 1 wherein:
   a. said core wire extends between first and second opposing ends;
   b. said first connector means joining said plurality of peripheral wires together and fixedly securing the first end of said core wire thereto; and
   c. a plurality of legs extend from said second connector means generally toward the second end of said core wire and spaced about said core wire, each of said legs having a first end coupled to said second connector means and a second end opposite the first end, the second end of each of said plurality of legs having a foot for engaging an interior wall of a blood vessel to maintain said blood clot filter at a desired location within said blood vessel, and to maintain said blood clot filter centered within said blood vessel.

9. The blood clot filter recited by claim 8 wherein the second end of said core wire extends beyond the second ends of said plurality of legs and terminates in a retractor fitting for releasably engaging a retractor to pull said first connector means toward said second connector means as said core wire slides through said second connector means.

10. The blood clot filter recited by claim 1 wherein:
  a. said core wire extends between first and second opposing ends;
  b. said first connector means joining said plurality of peripheral wires together and fixedly securing the same to the first end of said core wire; and
  c. a plurality of legs extend from said first connector means generally away from the second end of said core wire and spaced about said core wire, each of said legs having a first end coupled to said first connector means and a second end opposite the first end, the second end of each of said plurality of legs having a foot for engaging an interior wall of a blood vessel to maintain said blood clot filter at a desired location within said blood vessel, and to maintain said blood clot filter centered within said blood vessel.

11. The blood clot filter recited by claim 8 wherein the wire portion extending between said first and second connector means for each of said plurality of peripheral wires is of a predetermined length, and wherein said core wire is of a length greater than said predetermined length, the second end of said core wire terminating in a retractor fitting for releasably engaging a retractor to maintain said first connector means fixed while said second connector means is advanced toward said first connector means by sliding said second connector means along said core wire.

12. The blood clot filter recited by claim 1 wherein said plurality of peripheral wires includes at least six peripheral wires spaced substantially equiangularly about said core wire.

13. The blood clot filter recited by claim 1 wherein said core wire and said plurality of peripheral wires are made of stainless steel.

14. The blood clot filter recited by claim 1 wherein said core wire and said plurality of peripheral wires are made of titanium.

15. The blood clot filter recited by claim 1 wherein the thicknesses of said peripheral wires forming said filter mesh are each approximately 0.010 inch.

16. The blood clot filter recited by claim 1 wherein the flattened filter mesh formed by said plurality of peripheral wires extends generally perpendicular to the central longitudinal axis of said blood clot filter.

17. In combination, a blood clot filter and a filter delivery apparatus, wherein:
  a. said blood clot filter comprises in combination:
    i. a core wire extending along a central longitudinal axis of said blood clot filter and including first and second opposing ends;
    ii. a plurality of peripheral wires extending generally about and spaced around said core wire;
    iii. a first connector for connecting together said plurality of peripheral wires at a first connection point, said core wire lying within said plurality of peripheral wires at said first connection point and fixedly securing said plurality of peripheral wires to the first end of said core wire;
    iv. a second connector for connecting together said plurality of peripheral wires at a second connection point spaced apart from said first connection point and slidingly securing said plurality of peripheral wires about said core wire lying therein;
    v. locking means permitting said second connector to slide along said core wire from a first remote position to a second proximate position, said locking means preventing said second connector from sliding along said core wire from said second proximate position back to said first remote position; and
    vi. said plurality of peripheral wires each including a wire portion extending between the first and second connectors and lying generally along said core wire when said second connector is in said first remote position, said wire portions moving radially away from said core wire to a deployed position for forming a generally flattend filter mesh as said second connector advances to its second proximate position;
  b. said filter delivery apparatus comprises in combination:
    i. a delivery catheter having a distal end for percutaneous introduction into a blood vessel and having a proximal end opposite the distal end thereof, the distal end of said delivery catheter being adapted to receive said blood clot filter for positioning the same at a desired location in a blood vessel;
    ii. a pusher catheter slidingly received within said delivery catheter and having a distal end proximate the distal end of said delivery catheter, said pusher catheter having a proximal end extending from the proximal end of said delivery catheter, the distal end of said pusher catheter abutting said blood clot filter for advancing the same out of the distal end of said delivery catheter; and
    iii. a retractor cable slidingly extending through said pusher catheter, said retractor cable having a proximal end extending outwardly from the proximal end of said pusher catheter and having a distal end releasably coupled to the second end of said core wire of said blood clot filter for retracting said core wire after said blood clot filter is at least partially advanced from the distal end of said delivery catheter while said pusher catheter remains in abutting relationship with said blood clot filter for causing said plurality of peripheral wires to form said filter mesh.

18. The combination recited in claim 17 wherein said filter delivery apparatus further includes an outer catheter having a distal end for percutaneous introduction into a blood vessel and having a proximal end opposite to the distal end thereof, said outer catheter slidingly receiving said delivery catheter for allowing said blood clot filter to be delivered thereby, said outer catheter including an entrance port at the proximal end thereof, said entrance port including a deformable seal for sealing the proximal end of said outer catheter while permitting the distal end of said delivery catheter to be removably inserted therethrough.

19. The combination recited in claim 17 wherein each of said plurality of peripheral wires includes a leg portion extending from one of said first and second connectors in a direction generally opposite to the other of said first and second connectors, each of said leg portions being biased away from the central longitudinal axis of said blood clot filter, each of said leg portions having a foot at an end thereof for engaging an interior wall of a blood vessel to maintain said blood clot filter at a desired location within said blood vessel.

* * * * *